United States Patent
Ogusu

(10) Patent No.: US 9,506,870 B2
(45) Date of Patent: Nov. 29, 2016

(54) FLOW-CHANNEL DEVICE FOR DETECTING LIGHT EMISSION

(71) Applicant: CANON KABUSHIKI KAISHA, Tokyo (JP)

(72) Inventor: Makoto Ogusu, Shimotsuke (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/926,679

(22) Filed: Jun. 25, 2013

(65) Prior Publication Data

US 2014/0024126 A1    Jan. 23, 2014

(30) Foreign Application Priority Data

Jul. 18, 2012   (JP) ................... 2012-159793

(51) Int. Cl.
| | |
|---|---|
| *G01N 21/75* | (2006.01) |
| *G01N 21/05* | (2006.01) |
| *B01L 3/00* | (2006.01) |
| *G01N 21/00* | (2006.01) |

(52) U.S. Cl.
CPC ......... *G01N 21/75* (2013.01); *B01L 3/502707* (2013.01); *G01N 21/05* (2013.01); *B01L 2200/0689* (2013.01); *B01L 2300/0816* (2013.01); *B01L 2300/168* (2013.01); *G01N 2021/056* (2013.01); *G01N 2201/064* (2013.01); *Y10T 436/143333* (2015.01)

(58) Field of Classification Search
CPC .......... G01N 21/05; G01N 2021/056; G01N 2201/064; G01N 21/75; Y10T 436/143333; B01L 2200/0689; B01L 2300/0816; B01L 2300/168; B01L 3/502

USPC ....... 422/68.1, 82.05, 502; 436/94; 257/618; 216/10; 435/6.12

See application file for complete search history.

(56) References Cited

U.S. PATENT DOCUMENTS

| | | | |
|---|---|---|---|
| 2006/0057708 A1 | 3/2006 | Takamura et al. | |
| 2007/0099290 A1* | 5/2007 | Iida ................... | B01L 3/502707 435/287.2 |

(Continued)

FOREIGN PATENT DOCUMENTS

| | | |
|---|---|---|
| JP | 2002-286627 A | 10/2002 |
| JP | 2006-053094 A | 2/2006 |

(Continued)

OTHER PUBLICATIONS

Notification of Reason for Refusal in Japanese Application No. 2012-159793 (dispatched May 6, 2016).

*Primary Examiner* — Rebecca M Fritchman

(74) *Attorney, Agent, or Firm* — Fitzpatrick, Cella, Harper & Scinto

(57) ABSTRACT

The present invention provides a flow-channel device for detecting light emission, which suppresses a noise originating in unnecessary light emission, and can be simply bonded with the use of an organic material. The flow-channel device having a flow channel is structured by the bonding of at least two substrates, wherein at least any one substrate has a first groove which constitutes the flow channel, and a second groove for arranging an adhesive therein which contains an organic material, and a light-shielding layer is provided on an inner wall of the second groove so as to block a light emitted from the second groove from penetrating into the first groove.

20 Claims, 6 Drawing Sheets

(56) References Cited

U.S. PATENT DOCUMENTS

2008/0254997 A1* 10/2008 Oku et al. .................. 506/9
2008/0296734 A1* 12/2008 Momose .................. 257/618
2009/0202391 A1*  8/2009 Hagiwara et al. ........... 422/68.1
2013/0168250 A1*  7/2013 Fogleman et al. ............ 204/547

FOREIGN PATENT DOCUMENTS

| JP | 2006-078414 A | 3/2006 |
| JP | 2010-043928 A | 2/2010 |
| WO | 2007/099736 A1 | 9/2007 |

* cited by examiner

FLOW-CHANNEL DEVICE FOR DETECTING LIGHT EMISSION

BACKGROUND OF THE INVENTION

Field of the Invention

The present invention relates to a flow-channel device using a light-emission detecting method.

Description of the Related Art

A μ-TAS (Micro Total Analysis system) means a device or the like which uses a fine reaction field therein that is produced by the application of a lithography process and a thick film process technology, and is used for detecting as small an amount as a sample of nanoliter scale or subjecting the same to the reaction. In recent years, the μ-TAS is used in chemical analysis, reagent preparation, chemical synthesis, reaction detection and the like. A representative μ-TAS includes, for instance, a DNA chip, a Lab on a Chip, a microarray and a protein chip. The μ-TAS is used for medical inspection/diagnosis, and is applied to: a region of a genetic test, a chromosomal test, a cytoscopy and the like; a biotechnology; a test of a trace amount of a substance in an environment; an investigation on a farming environment of an agricultural product and the like; a genetic test for an agricultural product; and the like.

In a conventional inspection method, a process and an operation of equipment to be used are complicated, and a skillful operation is needed. Accordingly, these inspections have been mainly conducted while relying on the manipulation of a laboratory technician. However, when the μ-TAS is used, automation is enabled, and anyone can easily conduct the inspection. In addition, the μ-TAS also brings about various effects such as an increase of the speed, an increase of the accuracy, a reduction of the cost, a reduction of the period of time needed, and a reduction of the environmental impact.

In the μ-TAS, a flow channel and a detection of emitted light such as the measurement of fluorescence are occasionally used in combination. On this occasion, the amount of an object to be inspected is so trace that it is occasionally necessary to reduce the light which is emitted from another substance than a liquid to be inspected and causes a noise.

Methods for suppressing the light emission which causes the noise in a device using a flow channel are disclosed in Japanese Patent Application Laid-Open No. 2006-078414 and Japanese Patent Application Laid-Open No. 2002-286627. In Japanese Patent Application Laid-Open No. 2006-078414, a light-shielding portion is provided on the surface of a substrate along the flow channel, and the light-shielding portion shields the fluorescence which is emitted from the substrate. In Japanese Patent Application Laid-Open No. 2002-286627, a flow-channel device is disclosed which is formed by using an adhesive and has a light-shielding layer therein.

In the invention disclosed in Japanese Patent Application Laid-Open No. 2006-078414, a flow channel is produced by a joining method such as hot press which does not use an adhesive. In order to practice such a joining method, such conditions are needed that surfaces of substrates or the like to be joined are completely flat or can be sufficiently deformed by an action from the outside when being joined (that substrate is resin, or the like), as is shown in the cross-sectional view which is illustrated in FIG. 1B in Japanese Patent Application Laid-Open No. 2006-078414.

Specifically, when a brittle material such as quartz is used, after the light-shielding portion has been formed, the surface to be joined needs to be flattened. In order to flatten the surface to be joined, a method is considered which includes film-forming the light-shielding portion, then forming another material so as to become thicker than the light-shielding portion, and then polishing the surface; or a method is considered which includes firstly removing a part of the plate substrate corresponding to the thickness of the light-shielding portion by some process, forming a light-shielding film, and then polishing the surface to remove an unnecessary portion and flatten the surface. However, any method is complicated and has been disadvantageous also in the point of the cost.

Japanese Patent Application Laid-Open No. 2002-286627 discloses a flow-channel device having a light-shielding layer therein. However, in this application, a procedure of producing a flow-channel device is not disclosed. In addition, a pattern of the light-shielding film layer is not formed in consideration of an assembling operation necessary when the flow-channel device is used.

SUMMARY OF THE INVENTION

In order to solve the above described problems, an object of the present invention is to provide a flow-channel device for detecting light emission, which reduces an influence of a noise originating in such a situation that unnecessary light emission reaches a detecting unit, and can be produced simply by a bonding process with the use of an organic material.

Further features of the present invention will become apparent from the following description of exemplary embodiments with reference to the attached drawings.

DESCRIPTION OF THE EMBODIMENTS

Figure 1A:
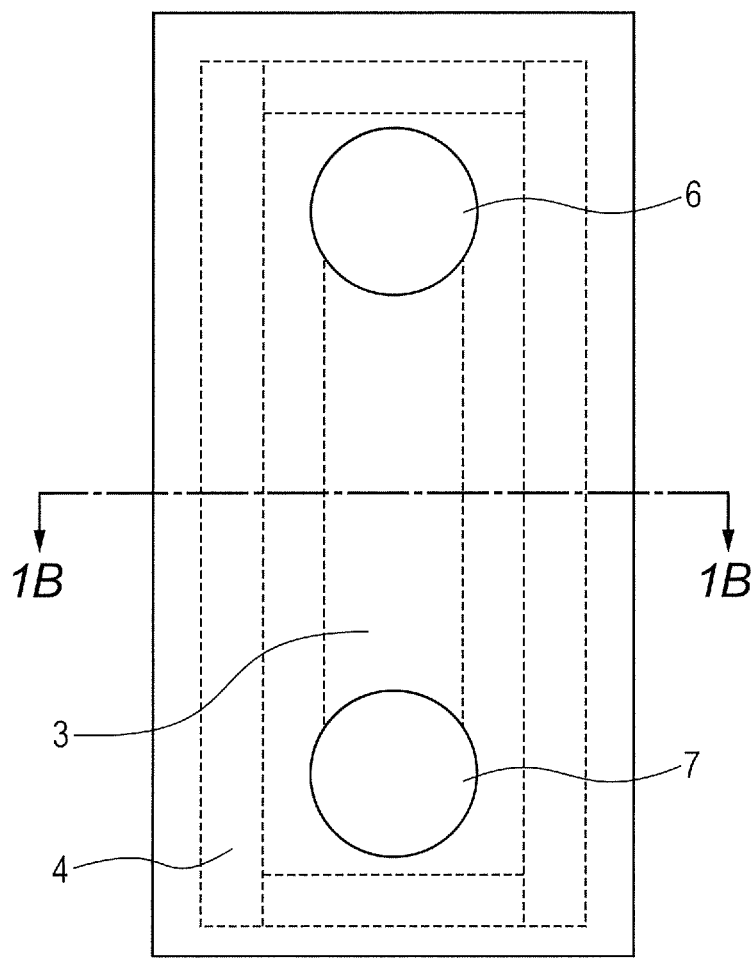
FIG. 1A and FIG. 1B are a top plan view and a cross-sectional view schematically illustrating a flow-channel device, respectively.

Preferred embodiments of the present invention will now be described in detail in accordance with the accompanying drawings.

In order to cope with the above described problems, the present invention provides a flow-channel device having a flow channel which is structured by bonding of two substrates, wherein at least any one substrate has a first groove which constitutes the flow channel, and a second groove which contains an adhesive therein that contains an organic material, and the second groove has a light-shielding film provided on an inner wall thereof.

The present invention also provides the flow-channel device, wherein the second groove is arranged further so as to surround the first groove, when viewed from a direction perpendicular to the flat surface of the substrate.

The present invention further provides the flow-channel device, wherein the shape of the second groove in a cross section of the substrate is a curve. This feature makes the film thickness of the light-shielding film uniform.

The present invention further provides a method for manufacturing the flow-channel device, in which the first groove and the second groove are formed with the same processing method.

The present invention still further provides the flow-channel device, wherein the light-shielding film is a metal film.

The present invention provides a flow-channel device having a flow channel which is structured by bonding of two substrates, wherein a first substrate has a first groove which constitutes the flow channel, and a second groove which contains an adhesive therein that contains an organic material, and the second groove has a light-shielding film provided on an inner wall thereof.

The flow-channel device means a device using a flow channel, and refers to a device using a flow channel, which is used in chemical analysis, reagent preparation, chemical synthesis, reaction detection, a genetic test, a chromosomal test, a cytoscopy, a biotechnology, a test of a trace amount of a substance in an environment, and the like. The flow channel refers to a tubular shape in which a sample, a solvent, a solvent containing a sample, a gel, a sol or the like flows.

The material of the substrate is not limited in particular, as long as the material is excellent in stability. An inorganic glass material such as quartz, Pyrex and TEMPAX can be used as a suitable example. The substrate can be a transparent material having optical transparency.

The organic material refers to a material of which the raw material is an organic compound, and particularly refers to an organic compound or the like which has adhesiveness when having been arranged on the two substrates. Usable adhesives containing the organic material include: dehydration condensation reaction type of and addition polymerization type of silicone rubbers; and adhesives containing the organic compound such as Teflon, polyethylene, polypropylene, polyvinyl chloride, polystyrene, a polymethyl methacrylate resin (PMMA), polycarbonate, an AAS resin, a room temperature setting acrylic adhesive and an anaerobic adhesive. However, such a material should be selected as to give little influence when the material has leaked to the flow channel. The adhesive can be an adhesive which discharges little gas in a degasification process or the like and little dissolves in the liquid in the flow channel, and an SB film (product made by Yamanaka Semiconductor Co., Ltd.) or the like can be used. However, if a substance or the like for preventing the dissolution (for instance, the above described SB film) is arranged between the flow channel and the adhesive, a selection range of a usable adhesive is widened.

The inner wall of the groove refers to a wall inside of the groove. The light-shielding film refers to a film which does not transmit light therethrough.

Figure 1B:
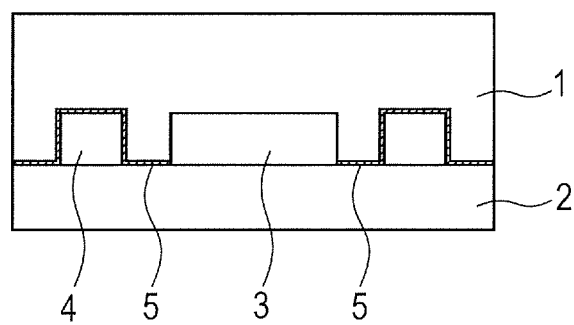

FIGS. 1A and 1B are views schematically illustrating a flow-channel device of the present invention, FIG. 1A is a top plan view, and FIG. 1B is a cross-sectional view when viewed from the cross section taken along the line 1B-1B in FIG. 1A.

This flow-channel device is structured by the bonding of a first substrate 1 and a second substrate 2. The first substrate 1 has a groove 3 which constitutes a flow channel, and a groove 4 for arranging an adhesive therein which contains an organic material. When the two substrates are bonded to each other, the groove 3 becomes a flow channel. A light-shielding layer 5 is arranged on the inner wall of the above described second groove so as to block light emitted from the groove 4 from penetrating into the above described first groove 3. Thereby, an influence of light emission from the organic material contained in the adhesive filled in the groove 4 can be neglected. Because of this, in the flow-channel device of the present invention, a wide variety of organic materials can be used as the adhesive.

Apertures 6 and 7 are provided on the first substrate, which penetrate the first substrate, communicate with the first groove 3 that is the flow channel, and become a supply port of the liquid to and a discharge port of the liquid from the flow channel.

In order that the external detecting unit detects the light emitted in the flow channel, any one substrate can have optical transparency, and a surface opposing to the flow channel can be determined to be a detecting surface.

For instance, the first substrate 1 can be a transparent quartz glass, and the upper face of the first substrate can be determined to be the detecting surface for detecting the light emitted in the flow channel. In this case, the light-shielding layer 5 is arranged in the second groove 4. Accordingly, even when the organic material arranged in the second groove emits light, the light does not penetrate into the flow channel which is formed of the first groove 3, and accordingly does not exert an influence on the detection.

The light-shielding layer 5 may be arranged in the inner wall of the above described second groove so as to block the light emitted from the second groove 4 from penetrating into the above described first groove 3. When the light-shielding layer 5 is arranged to wholly cover the detecting surface (upper face of substrate) so as to cover the second groove as is illustrated in FIGS. 1A and 1B, the light emitted from the organic material arranged in the second groove results in being not detected through the detecting surface. Thereby, the flow-channel device can suppress the noise which may occur when the light emission in the flow channel is detected.

However, if a light source has such a structure as to be capable of selectively irradiating the inside of the flow channel with light and a light detector also has such a structure as to be capable of selectively detecting only the light emitted in the flow channel, the second groove does not need to be wholly covered as is illustrated in FIGS. 1A and 1B. In this case, the light-shielding layer 5 is arranged only in a portion which is arranged between the first flow channel 3 and the second flow channel 4 and can block the transmission of the light, and may not be arranged in the upper face portion of the groove 4 and a portion of the wall face which is the opposite side to the flow channel.

The present invention also provides the flow-channel device which has a second groove arranged therein so as to surround the first groove when viewed from a direction perpendicular to the flat surface of the substrate.

Figure 3:
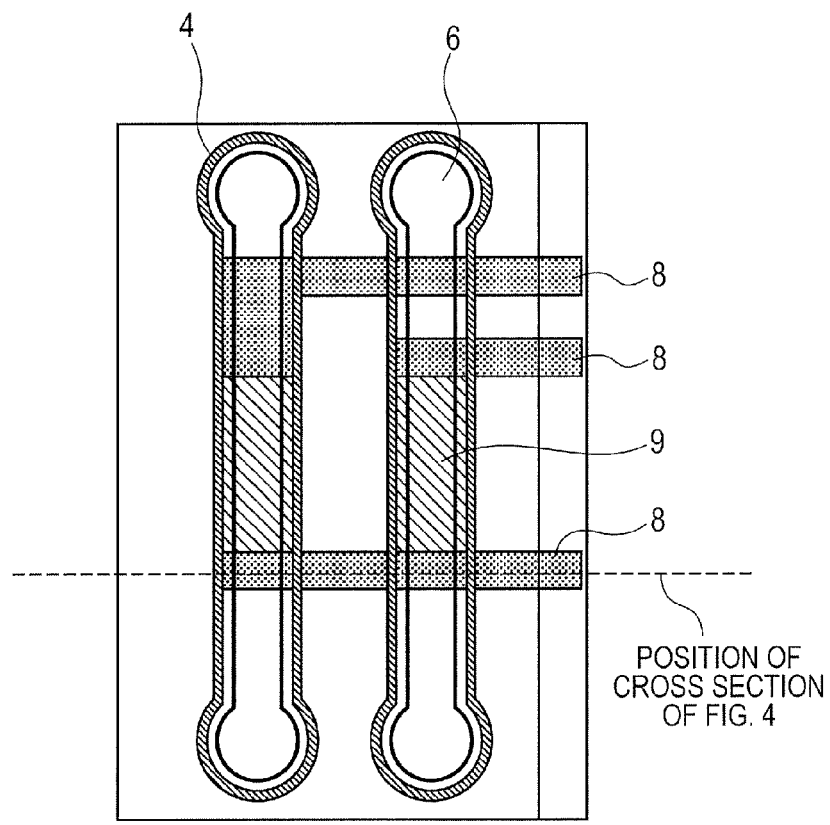
FIG. 3 is a view for describing the arrangement of each pattern of the flow-channel device.

Specifically, as is illustrated in FIG. 3, the second groove 4 can be arranged so as to surround the flow channel 3 when viewed from a direction perpendicular to the substrate. When having such a structure as to surround the flow channel, the second groove can reduce the leakage of the liquid in the flow channel to the outside through a gap between the bonded surfaces. When a plurality of the flow channels is collocated, in particular, the arrangement can reduce the influence of the flow channels and suppress the mixture of the liquid, which is desirable. In addition, when the second groove 4 is arranged so as to surround the flow channel, the light-shielding film surrounds the flow channel, and accordingly can block the light which might have come into the flow channel from the side face of the substrate.

In addition, in the second groove 4 in the present invention, the shape in the cross section of the substrate is formed in a curve. The description that the shape in the cross section is formed in a curve means that the shape of the groove in the cross section does not include a right angle or an acute angle, and can be a shape which has been formed by isotropic etching from the flat surface of the substrate. Due to the shape of the groove in the cross section of the substrate being formed from a curve, the above described flow-channel device can be provided without the film thickness of the light-shielding film becoming partially thin when the light-shielding film is formed.

The present invention also provides the flow-channel device in which the light-shielding film formed in the second groove 4 is a metal film. When the metal film is used, the production process is highly compatible with an existing semiconductor process, and the metal film can adequately keep light-shielding properties even by the thin film. Examples of the material of the metal film include Al, Ta and Ni, and particularly metallic chromium.

The present invention also provides a method for manufacturing the flow-channel device, which includes the steps of: forming the first groove and the second groove in the first substrate; forming the light-shielding film in the second groove; arranging the adhesive in the second groove; and bonding the first substrate and the second substrate to each other with the adhesive arranged in the second groove.

The present invention also provides a method for manufacturing the flow-channel device, in which the second groove is formed by wet etching. The wet etching means etching with a liquid. In the wet etching process, a pattern can be processed by masking.

The present invention also can form the first groove and the second groove with the same processing method. Specifically, the present invention provides a method for manufacturing the flow-channel device, which includes forming the first and second grooves by dry etching. The dry etching means a method of etching the substrate with gas or ions.

Furthermore, the present invention provides a method for manufacturing the flow-channel device, in which the first groove is further etched after the light-shielding film has been formed in the second groove.

The present invention provides also a DNA inspection apparatus which includes: the flow-channel device; a light source for irradiating the flow-channel device with light; a light detector which detects a light emitted from the flow-channel device; a circuit for supplying an electric current to a heat-generating resistor; and a unit which makes a liquid move in a flow channel of the flow-channel device. The DNA inspection apparatus refers to an apparatus which is used for a genetic test, a chromosomal test and the like, and conducts inspection using DNA as a sample. The heat-generating resistor means a mechanism which generates heat when an electric current has been passed in the resistor, and a platinum heater can be taken as an example.

The present invention provides also a DNA inspection system which uses the DNA inspection apparatus. The DNA inspection system refers to a system which conducts inspection using DNA as a sample.

The present invention provides also an inspection method of DNA using the flow-channel device, which includes the steps of: passing a liquid containing DNA into the flow channel; and detecting a light emitted from the liquid in the flow channel.

The flow-channel device of the present invention does not need to use a flattening treatment step which is complicated and requires accuracy, and can easily join the substrates to each other through an adhesive, even though each of the substrates has a surface on which a complicated step height such as a wiring pattern exists. On the other hand, the second groove has the light-shielding film therein, and accordingly suppresses the generation of the fluorescence from the adhesive containing the organic material. Furthermore, the region in which the adhesive is arranged is away from the flow channel, and accordingly the leakage of the organic material to the liquid in the flow channel is reduced to be a minimum.

The amount of the fluid which exudes from a groove to another groove through the gap formed between the bonded surfaces varies depending on the degree of the unevenness on the surfaces of the substrates to be bonded. If the smoothness of each of the surfaces is high, the penetration of the liquid into the second groove can be substantially prevented, but when each of the grooves is formed so as to be away from each other, the area of the portion at which the adhesive and the liquid in the flow channel come in contact with each other can be further reduced. In addition, such a point is also a feature of the present invention that the flow-channel device can be achieved by a simple process of forming the two grooves.

In addition, the method for processing the groove can be appropriately selected, and accordingly the flow-channel device of the present invention is excellent in productivity.

Furthermore, when the method of forming the first groove and the second groove with the same processing method is employed, the flow-channel device can be more efficiently produced.

The present invention will be described in detail below with reference to exemplary embodiments.

[Exemplary Embodiments]

In the present exemplary embodiment, a device will be described below as an example, which is used in medical inspection and the like using such a reaction that when a reagent is introduced into a fine flow channel and is continuously heated therein, the amount of light emitted in the reagent varies. Incidentally, the emitted light includes fluorescence or chemiluminescence.

[Exemplary Embodiment 1]

A heater metal which generates heat is provided closely to the flow channel into which the reagent is introduced, as a unit for continuously heating the reagent. Thereby, the reagent can be quickly and stably heated. At the same time, platinum is used for the heater which generates heat and the resistance value is measured. Thereby, the temperature of a heating body is detected from the physical constant. Thereby, it can be known at what temperature of the reagent the measured amount of the fluorescence has been emitted. Platinum is patterned directly under the flow channel so that more accurate temperature is measured. Gold is patterned so as to secure energy supply to the platinum and electrical contact with the platinum. The pattern using the gold is continuously formed up to an opened part in which the substrate for the flow channel is partially removed.

Figure 2:
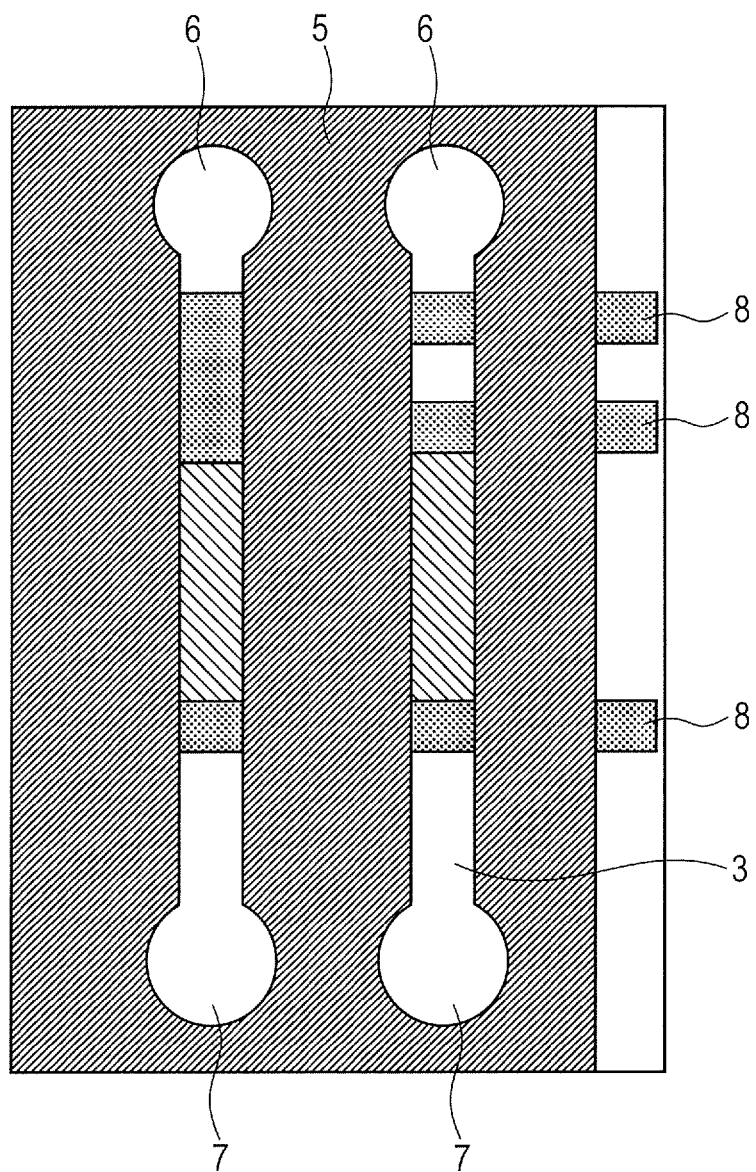
FIG. 2 is a view observed from the upper face of the flow-channel device.
Figure 4:
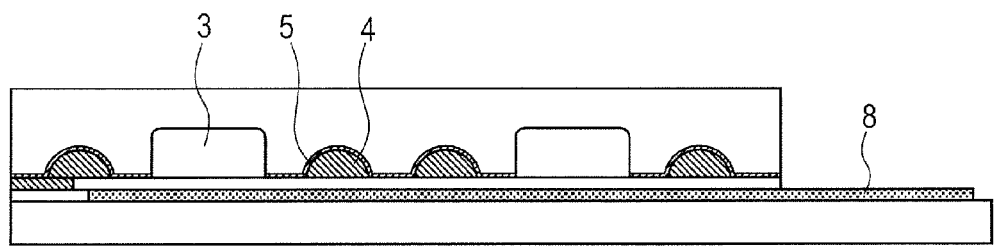
FIG. 4 is a cross-sectional view of the flow-channel device.

FIG. 2 illustrates a view observed from the upper face of the flow-channel device; and in order to describe the arrangement of each pattern of the flow-channel device, FIG. 3 illustrates a state in which a light-shielding film is seen through, and FIG. 4 illustrates the cross section including the flow channel. FIG. 4 is a cross-sectional view of the flow-channel device when viewed from a direction orthogonal to the flow channel. In FIGS. 2 to 4, a light-shielding film 5, an electroconductive pattern 8 in which the pattern of gold is exposed on the surface so that voltage can be easily applied from the outside, a flow channel 3 which is formed of a first groove, and a heat-generating resistor (heater) 9 which is formed from platinum or the like are shown.

As is illustrated in FIG. 2, the flow-channel device has two flow channels 3 each having an introduction port and a discharge port 6 and 7 for introducing the reagent thereinto and discharging the reagent therefrom, respectively, when viewed from the upper face. Platinum which becomes the heater 9 is patterned in the center of the flow channel 3. FIG. 3 is a view for describing a positional relationship among the heater 9, the electroconductive pattern 8 and the flow channel 3, when the light-shielding film 5 is seen through. The electroconductive pattern 8 is connected to both ends of the heater 9, and the heater 9 exists in a part of the flow channel 3. The electroconductive pattern 8 which is connected to the heater 9 is patterned so as to cross the flow channel 3, and is arranged on the surface exposed at the portion from which the substrate for the flow channel has been removed, as the electroconductive pattern 8 for securing electric conduction. A transparent substrate having high optical transparency is used for the substrate in the upper face side of the flow channel 3 so as to transmit fluorescence emitted from the flow channel to the outside therethrough.

In the present exemplary embodiment, quartz was used for the two substrates, which is excellent in thermal stability and chemical stability. The material can be replaced by another material with an equivalent function in optical transparency and the like. The material includes, for instance, Pyrex (trade name) and TEMPAX (trade name). On the other hand, the heat-generating resistor of platinum and the electroconductive pattern of gold have limited thicknesses, as are illustrated in FIGS. 3 and 4. If both of the substrates are brought into close contact with each other while having the step heights corresponding to these thicknesses, a gap due to the step heights results in the middle of the flow channel. The outflow (or inflow) of the reagent through the gap causes the contamination of the liquid in a space between the flow channels, and accordingly must be particularly avoided.

In the present exemplary embodiment, an adhesive containing an organic material was used for integrating the two substrates. Because the adhesive fills the gap containing the step heights, the two substrates could be integrated without causing a gap even when the substrates having the step heights were joined to each other.

The second groove 4 surrounding a flow channel which is the first groove is filled up with an adhesive. The second groove surrounds the first groove when viewed from a direction perpendicular to the flat surface of the substrate. A light-shielding film 5 is formed on an inner wall of the second groove, and accordingly prevents an adhesive from being irradiated with excitation light due to reflection or the like even when the light source does not directly irradiate the adhesive. Thereby, a flow-channel device could be structured which adequately reduced noise light when detecting fluorescence.

Furthermore, the adhesive was formed so as to have a predetermined shape on the first substrate and was accommodated in the second groove having approximately the same shape as the adhesive. Thus structured flow-channel device could remarkably reduce a contact area of the adhesive with a fluid in the flow channel compared to a case where the adhesive 7 constituted a part of the side wall of the flow channel, and could stably conduct the reaction.

[Exemplary Embodiment 2]

Next, a procedure for manufacturing the flow-channel device of the present exemplary embodiment will be described. The manufacturing procedure will be described below with reference to cross-sectional views of the single flow-channel device. However, the manufacturing was actually performed in a form of a wafer, and each flow-channel device was prepared by finally being cut out from the wafer.

Figure 6:
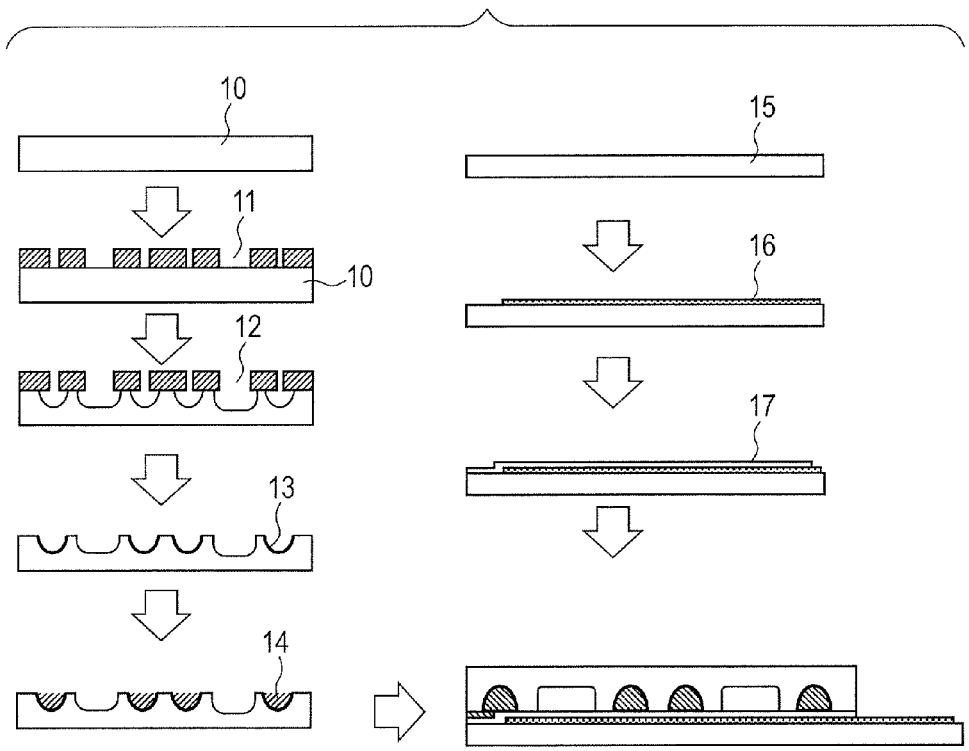
FIG. 6 is a view for describing a procedure for producing the flow-channel device.

FIG. 6 is a view for illustrating the manufacturing procedure. A quartz substrate 10, an opening pattern 11 of a cured resist and a recess part 12 containing an organic material are shown.

A photosensitive resist is firstly formed on the quartz substrate 10 in which a recess part that becomes a flow channel will be formed. The opening pattern 11 is formed on the site that becomes the flow channel 3 with the use of a photolithographic technology, and an etching mask from which the photosensitive resist has been removed is formed. The substrate having the opening patterned thereon is subjected to wet etching, and the recess part 12 is formed.

In wet etching, the etching progresses isotropically. Accordingly, the groove which had a cross-sectional shape formed from a curved plane could be formed. The cross-sectional shape was thus formed from the continuous plane, and thereby the problem could be reduced that a film thickness or a film itself became extremely discontinuous in a subsequent film-forming process.

Next, a light-shielding film 13 is formed on the inner wall of the second groove. A metal film (here chromium film) is formed on the front face of the substrate. The light-shielding film 13 formed of the metal film could be formed only on the inner wall of the second groove after the metal film has been removed by etching.

After that, holes which would become an introduction port and a discharge port of a reagent were processed (not illustrated). Here, a groove, an aperture and the like may be processed in order to secure a region in which a metal pattern and a terminal come in contact with each other when the flow-channel device has been completed.

On the other hand, a pattern 17 of a heat-generating resistor of platinum and the metal pattern 16 were formed on the other substrate.

After the processing of both substrates has been completed, the adhesive 14 is applied to the substrate on which the recess part 12 that becomes the flow channel 3 has been processed. The reason why the adhesive is applied to the substrate on which the recess part 12 has been processed is based on a viewpoint of adequate workability. After the adhesive has been applied, a relative position of wafers is adjusted with the use of a not-illustrated alignment mark, and the wafers are joined with each other. The joined wafers were cut and divided, and individual flow-channel devices were formed. After this, the light-shielding film is further provided appropriately on the surface of the substrate.

[Exemplary Embodiment 3]

Figure 5:
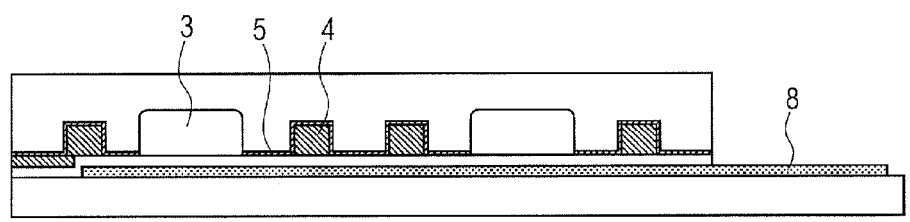
FIG. 5 is a flow-channel device produced by dry etching.

In the present exemplary embodiment, dry etching was used when the second groove was formed, as illustrated in FIG. 5. Because the dry etching is a processing method with high anisotropy, the opening pattern is formed so as to match the pattern of the second groove, with a photosensitive resist. Furthermore, the second groove was designed so as to have the same depth as that of the first groove which would become the flow channel. As a result, the first and the second grooves could be processed by one dry etching process, and the efficiency of the manufacturing process was enhanced.

[Exemplary Embodiment 4]
DNA Inspection System

Figure 7:
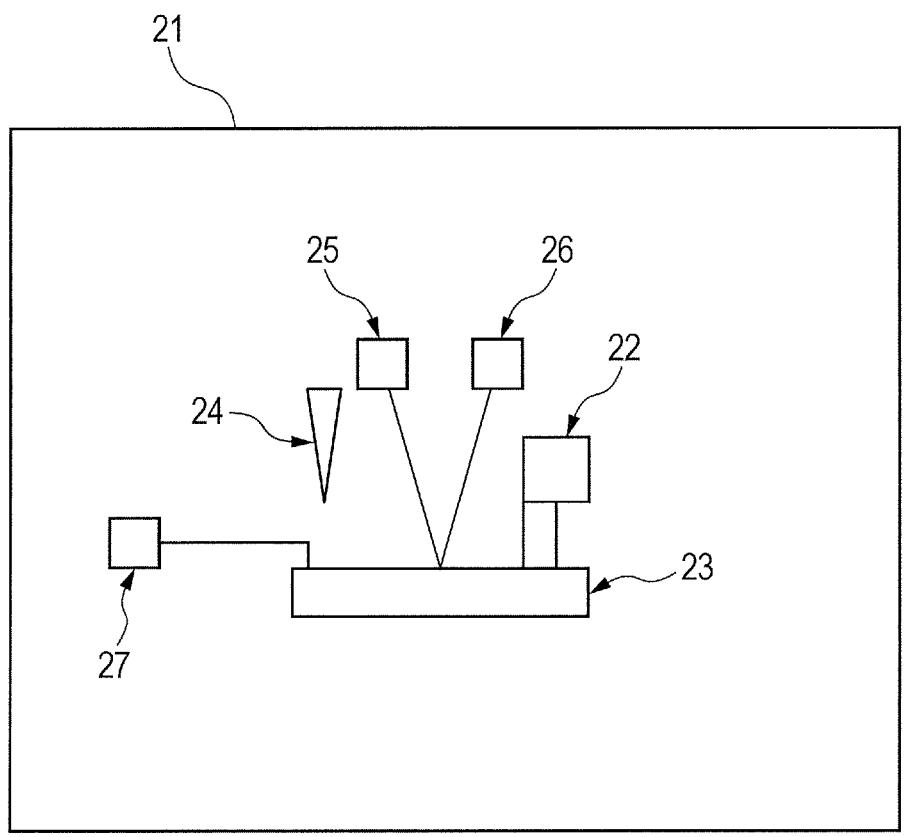
FIG. 7 is a view illustrating an inspection system using the flow-channel device.

A DNA inspection system using the flow-channel device which has been formed in the above described exemplary embodiments will be described below with reference to FIG. 7.

The DNA inspection system according to the present embodiment includes the flow-channel device and the DNA inspection apparatus.

The DNA inspection apparatus includes: a light source for irradiating the flow-channel device with light; a light detector which detects light emitted from the flow-channel device; a circuit for supplying an electric current to a heat-generating resistor; and a unit which makes a liquid move in the flow channel of the flow-channel device.

An inspection method of DNA using the flow-channel device in the present embodiment includes the steps of: passing a liquid containing DNA into the flow channel; and detecting a light emitted from the liquid in the flow channel, as will be shown below.

The DNA inspection apparatus 21 of the DNA inspection system includes: a mounting base for mounting the above described flow-channel device thereon, which is not illustrated; a light source for irradiating the flow-channel device with light; a light detector which detects light emitted from the flow-channel device; and a circuit for supplying an electric current to a heat-generating resistor.

If necessary, the inspection apparatus 21 includes: a pressure generator for passing the fluid in the flow channel; and a temperature measuring instrument for measuring the temperature of the fluid in the flow channel based on a resistance value of the heat-generating resistor.

The inspection apparatus 21 has the pressure generator 22 which generates a positive or negative pressure, as a unit which makes the liquid move in the flow channel of the flow-channel device. The pressure generator 22 is a pump such as a syringe pump, and is connected to a discharge port of the flow-channel device 23 to generate the pressure in the flow channel. In addition, a liquid introducer 24 such as a pipette is shown.

The light source 25 and the light detector 26 are combined to constitute the reaction-detecting unit. The reaction-detecting unit includes: the light source 25 which becomes a light irradiation unit for irradiating the flow-channel device 23, such as a laser and LED; and the light detector 26 such as a CCD image sensor and a CMOS image sensor. The circuit 27 is a power source for applying a voltage to the heat-generating resistor through an electroconductive member of the flow-channel device and passes an electric current thereto, and heating the inside of the flow channel. In addition, the inspection apparatus may be provided therein with the mounting base (not illustrated) which mounts the flow-channel device 23 thereon, and a computer as a controlling section which controls the devices.

The flow-channel device of the present invention can be used also as a one-chip fluorescence-detecting device which has a PCR amplification region having a reflective heat-generating resistor in the upstream side of the flow channel, and a thermal analysis region having another reflective heat-generating resistor in the downstream side of the flow channel.

In addition, the temperature measuring instrument provided therein as needed calculates a resistance value of the heat-generating resistor from an electric current value of the electric current which passes through the heat-generating resistor and a voltage value of the voltage which is applied to the heat-generating resistor, and measures the temperature of the fluid in the flow channel.

The inspection method according to the embodiment of the present invention includes: preparing such an apparatus 21 and flow-channel device 23; supplying the fluid to the flow channel of the flow-channel device; changing the temperature of the fluid in the flow channel by heating with the heat-generating resistor; and optically detecting the state of the fluid in the flow channel.

[Exemplary Embodiment 5]

Figure 8:
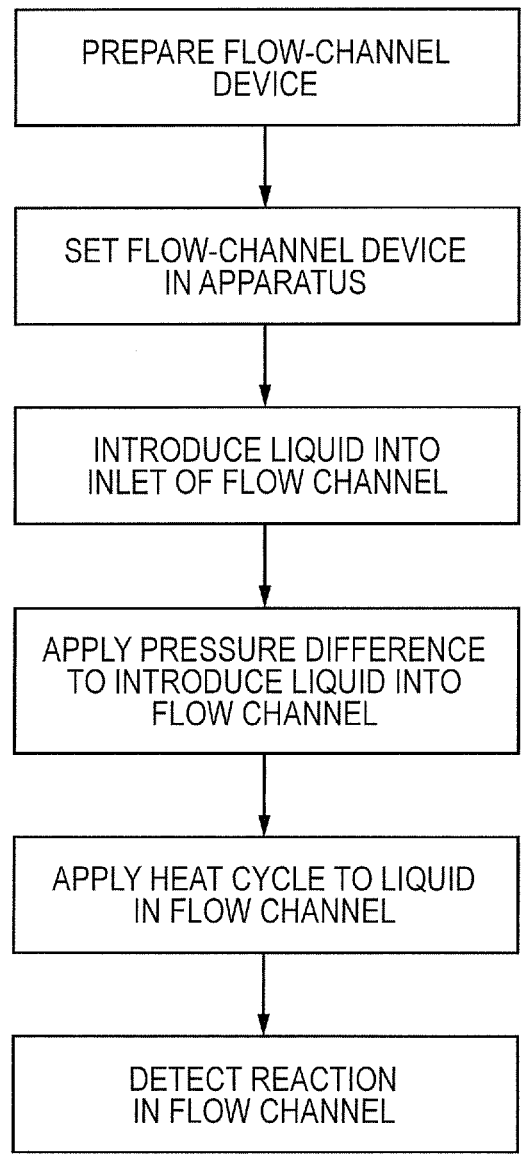
FIG. 8 is a view illustrating a flow chart of an inspection method using the flow-channel device.

FIG. 8 is a view of a flow chart of the inspection method which uses the above described apparatus. First, prepare the above described flow-channel device 23. Next, set the flow-channel device in a mounting section of the apparatus 21. Next, introduce the liquid such as a reagent or the like into an inlet of the flow channel (which has usually an aperture for supply) of the device, with the liquid introducer 24. After that, apply a pressure difference into the flow channel with a pressure generator 22 to introduce the liquid into the flow channel. Supply an electric power to the heat-generating resistor of the flow-channel device from the power source 27, and conduct the temperature control for changing the temperature of the liquid which has been introduced into the flow channel. The temperature control includes, for instance, the application of a temperature cycle which repeats temperature-raising and temperature-lowering for PCR, temperature-raising for measuring a thermal melting or the like. Optical detection of a reaction state of the liquid in the flow channel by using a reaction-detecting unit is performed, simultaneously with the temperature control or after the temperature control. As a result of the detection, the quantity of the reaction (including presence or absence of reaction) can be determined, and the reaction in the flow channel can be analyzed.

The DNA inspection system detects a light emitted from at least one part of the flow channel together with a light reflected from a reflecting face which is provided on the lower face of the inner wall of the flow channel, through the upper face of the inner wall and the observing face, by using the flow-channel device according to the present embodiment. At this time, one part or the whole of the heat-generating resistor generates heat, heats the fluid in the flow channel, and changes the temperature of the fluid. The DNA inspection system can conduct these processes in the same flow channel, accordingly can analyze the components in the liquid with high sensitivity and with the real time corresponding to the temperature change, and can conduct a suitable inspection.

In addition, the heat-generating resistor arranged on a wall surface of the flow channel can be used also as a temperature measurement instrument which measures the temperature in the flow channel based on the resistance value of the heat-generating resistor. The DNA inspection system can more accurately control the heating temperature by feeding back the measurement result to the power source.

The flow-channel device according to the present invention has the light-shielding layer arranged so as to block light from penetrating into the first groove which is the flow channel, and thereby an unnecessary light emission including light emitted from an organic material contained in the second groove does not reach the detecting unit. Accordingly, the flow-channel device can reduce the influence of the noise. The flow-channel device of the present invention also can be simply produced by the bonding with the use of an adhesive containing an organic material.

Furthermore, in the flow-channel device according to the present invention, the second groove exists so as to surround the first groove that is the flow channel, and the second groove has the light-shielding film therein. Thereby, the flow-channel device can remarkably block light that penetrates into the flow channel from the side face of the substrate.

A schematic view of the flow-channel device is illustrated as a top plan view FIG. 1A and a cross-sectional view FIG. 1B. FIG. 2 illustrates a view observed from the upper face of the flow-channel device of another embodiment; and in order to describe the arrangement of each pattern of the flow-channel device, FIG. 3 illustrates a state in which a light-shielding film is seen through, and FIG. 4 illustrates the cross section including the flow channel. FIG. 4 is a cross-sectional view of the flow-channel device when viewed from a direction orthogonal to the flow channel.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-159793, filed Jul. 18, 2012, which is hereby incorporated by reference herein in its entirety.

What is claimed is:

1. A flow-channel device having a flow channel which is structured by bonding of at least a first substrate and a second substrate,
wherein the first substrate has a first groove, which constitutes the flow channel, and a second groove, which does not constitute the flow channel,
wherein the first substrate and the second substrate are each made from an inorganic material,
wherein the second groove is filled with an adhesive that bonds the first substrate and the second substrate,
wherein the adhesive contains an organic material,
wherein the second groove has a light-shielding film provided on an inner wall thereof, and
wherein the first groove is next to, but is isolated from, the second groove.

2. The flow-channel device according to claim 1, wherein the second groove is arranged so as to surround the first groove, when viewed from a direction perpendicular to a flat surface of the first substrate.

3. The flow-channel device according to claim 1, wherein the second groove has a curved shape in a cross section of the first substrate.

4. The flow-channel device according to claim 1, wherein the light-shielding film formed in the second groove is a metal film.

5. A method for manufacturing the flow-channel device according to claim 1, comprising:
forming the first groove and the second groove in the first substrate;
forming the light-shielding film in the second groove;
arranging the adhesive in the second groove; and
bonding the first substrate and the second substrate to each other with the adhesive arranged in the second groove.

6. The method for manufacturing the flow-channel device according to claim 5, wherein the second groove is formed by wet etching.

7. The method for manufacturing the flow-channel device according to claim 5, wherein the first and second grooves are formed by dry etching.

8. The method for manufacturing the flow-channel device according to claim 5, wherein the first groove is further etched after the light-shielding film has been formed in the second groove.

9. A DNA inspection apparatus comprising:
the flow-channel device according to claim 1;
a light source for irradiating the flow-channel device with light;
a light detector which detects light emitted from the flow-channel device;
a circuit for supplying an electric current to a heat-generating resistor; and
a unit which makes a liquid move in the flow channel of the flow-channel device.

10. An inspection method of DNA using the flow-channel device according to claim 1, comprising:
passing a liquid containing DNA into the flow channel; and
detecting light emitted from the liquid in the flow channel.

11. The flow-channel device according to claim 1, wherein the first groove does not contain the adhesive.

12. The flow-channel device according to claim 1, wherein the first groove and the second groove, at least in part, are both linear and parallel each other.

13. The flow-channel device according to claim 12, wherein the device has two second grooves, and wherein the first groove is in-between the two second grooves.

14. The flow-channel device according to claim 1, wherein a heater is provided on a flow channel side of the second substrate.

15. The flow-channel device according to claim 1, wherein the device has at least two flow-channels in parallel to each other.

16. The flow-channel device according to claim 1, wherein the first groove does not contain the adhesive and does not have the light-shielding film.

17. The flow-channel device according to claim 1, wherein the first substrate has an observing face to observe a light from the flow channel.

18. The flow-channel device according to claim 3, wherein the first groove has a substantially rectangular shape in the cross section of the first substrate.

19. The flow-channel device according to claim 1, wherein a surface of the first substrate is in contact with a surface of the second substrate except for a portion that contains the first and second grooves.

20. The flow-channel device according to claim 1, wherein the adhesive is present only in the second groove.

* * * * *